(12) United States Patent
Mitchell

(10) Patent No.: US 6,210,730 B1
(45) Date of Patent: Apr. 3, 2001

(54) METHOD FOR TREATMENT OF CONTAINERIZED FOODS

(76) Inventor: Jerry L. Mitchell, P.O. Box 667, Livingston, TX (US) 77351

(*) Notice: Subject to any disclaimer, the term of this patent is extended or adjusted under 35 U.S.C. 154(b) by 0 days.

(21) Appl. No.: 09/318,161

(22) Filed: May 25, 1999

Related U.S. Application Data

(63) Continuation-in-part of application No. 08/622,746, filed on Mar. 27, 1996, now abandoned, which is a continuation-in-part of application No. 08/323,439, filed on Oct. 4, 1994, now Pat. No. 5,597,599, which is a continuation-in-part of application No. 07/880,869, filed on May 11, 1992, now Pat. No. 5,352,467, which is a continuation-in-part of application No. 07/510,947, filed on Apr. 19, 1990, now abandoned, which is a continuation of application No. 07/214,195, filed on Jun. 27, 1988, now abandoned, which is a division of application No. 07/094,384, filed on Sep. 8, 1997, now abandoned.

(51) Int. Cl.⁷ ..................................................... B65B 31/04
(52) U.S. Cl. ........................... 426/312; 53/432; 53/434; 53/512; 426/316; 426/320; 426/321; 426/326; 426/327; 426/332; 426/333; 426/335; 426/392; 426/393; 426/410; 426/418; 426/518; 426/524; 426/602
(58) Field of Search ..................................... 426/312, 316, 426/320, 321, 324, 326, 327, 332, 333, 335, 392, 393, 410, 418, 518, 524, 602; 53/432, 434, 512

(56) References Cited

U.S. PATENT DOCUMENTS

| | | | | |
|---|---|---|---|---|
| 3,851,080 | * | 11/1974 | Lugg et al. | 426/312 |
| 3,930,040 | * | 12/1975 | Woodruff | 426/312 |
| 4,548,852 | * | 10/1985 | Mitchell | 426/393 X |
| 4,919,955 | * | 4/1990 | Mitchell | 426/394 |
| 5,352,467 | * | 10/1994 | Mitchell et al. | 426/316 |
| 5,481,852 | * | 1/1996 | Mitchell | 53/432 |
| 6,054,161 | * | 4/2000 | Palmer | 426/312 |

OTHER PUBLICATIONS

Zhao, Y. et al. "Applications of Dynamic Modified Atmosphere Packaging Systems for Fresh Red Meats: Review". *Journal of Muscle Foods*, vol. 5, pp. 299–328 (1994).*

* cited by examiner

*Primary Examiner*—Leo B. Tentoni
(74) *Attorney, Agent, or Firm*—Sankey & Luck, L.L.P.

(57) ABSTRACT

A method for treating a perishable meat product including the steps of chilling the meat product to within a selected temperature range, exposing the chilled meat product to a chilled gas mixture containing a significant fraction of inert gas, and thereafter removing the chilled gas and exchanging that gas with a gas mixture containing a high oxygen fraction.

58 Claims, No Drawings

METHOD FOR TREATMENT OF CONTAINERIZED FOODS

CROSS REFERENCE TO RELATED APPLICATIONS

This application is a continuation-in-part of applicant's application Ser. No. 08/622,746 filed Mar. 27, 1996, now abandoned, which was a continuation-in-part of applicant's application Ser. No. 08/323,439, filed Oct. 4, 1994, now issued as U.S. Pat. No. 5,597,599 which was a continuation-in-part of application Ser. No. 07/880,869, filed May 11, 1992, now issued as U.S. Pat. No. 5,352,467 which was a continuation-in-part of application Ser. No. 07/510,947 filed Apr. 19, 1990, now abandoned, which was a continuation of application Ser. No. 07/214,195 filed Jun. 27, 1988, now abandoned, which was a divisional of application Ser. No. 07/094,384 filed Sep. 8, 1997, now abandoned. The disclosures of the aforementioned applications are herein incorporated by reference.

BACKGROUND OF THE INVENTION

1. Field of the Invention

The present invention is directed to the preservation of wrapped and/or sealed foodstuffs. More specifically, the present invention is directed to the treatment of a perishable meat product preparatory to retail display.

2. Description of the Prior Art

Contemporary packaging of perishable products, and especially meat products, envisions maintaining the product in a controlled atmosphere from the time it is prepared at the packer until it is purchased by the consumer. Methods and apparatus to accomplish these objectives have been disclosed in U.S. Pat. Nos. 4,919,955, 5,352,467 and 5,481,852.

Several disadvantages however, exist with respect to the presentation of modified atmosphere packaged products to the consumer. One such disadvantage occurs when the product is sealed in a rigid tray with a flexible cover or film type lid. In instances where an enriched oxygen or carbon dioxide mixture is introduced into the package prior to presentation to the consumer, as is the case to promote a desirable "bloomed" color indicative of oxymyoglobin, the product must be sized so as to only partially fill the package resulting in a remaining void fraction or "headspace". This is because meat products readily respire upon the addition of soluble gases (e.g. oxygen or carbon dioxide). When these soluble gases are introduced into the package, they are absorbed into the meat tissue. This absorption continues for a protracted period which is known as the product shelf life. At the end of the shelf life, the product assumes a brownish color indicative of metmyoglobin.

Upon exposure to oxygen, the myoglobin pigment of muscle tissue is oxygenated. Carbon dioxide is dissolved in the water phase of the meat product. This absorption of these soluble gases results in the collapse or partial collapse of the hermetically sealed package lidding film. If the product is not proportionally undersized, the lidding film will be so tightly drawn downward due to the absorption of oxygen and carbon dioxide that the film touches the product. In the event of a meat product, the area of contact between the film and the product terminates respiration and as a consequence the product adopts an unpalatable brownish color indicative of metmyoglobin.

To avoid this phenomena, marketers of sealed products packaged in a modified atmosphere have adopted a process whereby a void fraction is built into the package in an amount proportional to its anticipated shelf life. In instances with an anticipated shelf life of 10 to 12 days, the void fraction is as large as the volume reserved for the product itself. As might be expected, this proposed solution is both unattractive and economically impractical since packaging and shipping costs are disproportionate to the volume of product.

Other disadvantages associated with packaged products include lack of moisture retention, or "purge". Purge occurs when the product is subjected to contact pressures such as those common in transport or those associated with a plastic film vacuum package. Purge also occurs when the product is subjected to temperatures above 40° F. such as commonly occurs in the retailer display cabinet. Previously, no solutions have yet been proposed to address this phenomena.

SUMMARY OF THE INVENTION

The present invention addresses the above and other disadvantages associated with prior art packing and gas exchange systems.

The present invention contemplates a process by which liquid exudate is minimized while at the same time allowing a meat product to be positioned in a sealed container so as to minimize unused volume. In a preferred embodiment, this process includes a series of sequential steps comprising chilling the meat product to a selected temperature range either before of after it is placed and sealed within a container, introducing a chilled gas mixture containing a significant inert gas fraction into the container, and thereafter removing this chilled gas and exchanging that gas with a gas mixture containing a high oxygen fraction.

The present invention presents a number of advantages over the prior art. One advantage is the minimalization of liquid purge from a meat product which may be subsequently exposed to a variety of temperatures and conditions. A second advantage presented by the method of the instant invention is the ability to utilize a sealed product package which is of substantially the same dimensions as the meat product itself. In such a fashion, waste and unit cost is minimized.

Other advantages will become obvious in view of the following detailed description.

DETAILED DESCRIPTION OF THE PREFERRED EMBODIMENTS

In one embodiment of the present invention, a given product, e.g., a beef product, is prepared for shipment to a retail facility, e.g., a grocery facility, for ultimate presentation to the consumer. For obvious reasons, it is desired to maintain the maximum freshness of the meat product during the time it is transported from the slaughterhouse to the retail outlet. In such a fashion the product is afforded a maximum shelf life.

The first step of such a method is to seal the product in a fluid tight container while the product is exposed to an oxidizer, e.g., $O_3$, $F_2$, $H_2O_2$, $KMnO_4$, HOBr, HOCl, $Cl_2$, $ClO_2$, $O_2$, $Br_2$ or $I_2$. By exposure to one or a combination of such oxidizers, the microbial presence on the exterior of the product will be substantially reduced or even neutralized. Moreover, by sealing both the oxidizer and the product within the container, the residence time of the oxidizer may be strictly controlled.

To enhance the effectiveness of the oxidizer, it may be desirable, once the package is sealed, to introduce a higher concentration of the same or a different agent into the sealed package. To further enhance the effectiveness of such an oxidizer, it may also be desirable to change the pressure within the package beyond a single atmosphere. Still alternatively, it may be desirable to change the temperature of the meat product and thereby expedite the oxidation process within the sealed package. In one embodiment, the meat product may be chilled to between 26–36° F. In still a further embodiment, it may also be desirable to employ infrared or ultraviolet radiation to said product to inhibit microbial activity on a given product.

To ensure that the product is uniformly exposed to a given agent, e.g., an oxidizer, the package preferably includes a bottom tray which is provided with a series of raised knobs or ridges. To further ensure that the product receives maximum exposure to the agent, the package, once sealed, may also be vibrated or oscillated for a short period of time during the packaging or transport stage, so as to vary the contact zones between the raised knobs or ridges and the product.

While exposure of the product to an oxidizer is beneficial from the standpoint of eliminating most surface microbial activity, it is sometimes desirable to remove or reduce the oxidizer after a selected residence time. To ensure the effectiveness of the gas, a residence time may be employed to establish an average penetration of some 5–7 mm or, in the instance of a ground meat product, that residence time necessary to ensure complete penetration. The length of this residence time will depend on such factors as the nature of the product, the mass of the product, the fat content of the product, the water content of the product, the temperature at which the product has been maintained, and the identity and concentration of the oxidizer. Once this residence time has been achieved, it is desirable to externally activate or remove the oxidizer from the package without disrupting the sealed integrity of the package itself. This may be achieved by extracting the oxidizer through a septum valve or other similar resealable valve disposed in the package.

Once the oxidizing agent is withdrawn, it may be desirable to introduce a second agent into the package to further minimize microbial activity on the product, or to inhibit the growth of bacteria during product presentation. These agents may include a $CO_2$ content. In one preferred embodiment, a $CO_2$ content of at least 15% may be used in conjunction with an inert gas, e.g. nitrogen, or any of the noble gases. Still alternatively, other gases such as carbon monoxide may be used. In the instance of a meat product this gas mixture may be introduced at a temperature range of between 26–36° F. during the packing stage. Alternatively, an agent with an $O_2$ content may be preferred. Oxygen causes the meat product to "bloom", or assume a bright red color. This bright red color is generally indicative of the freshness of the meat product and is therefore desirable to the consumer.

Multiple variations of the above described technique may be employed with any number of different perishable products. For example, if it is desired to process a perishable fish or poultry product, it may be necessary to alter the above method to change the concentration of the agent and/or the residence time. Further, in the case of fish or poultry products, which tend to degrade at a much faster rate than do meat products, there is necessarily an increased emphasis on inhibiting bacterial growth during transportation and storage or the product preparatory to retail sale. Hence, it may be desirable to maintain a weak oxidizer within the package during the transportation and storage phases.

Aside from the above described deteriorative effects associated with bacterial spoilage, perishable products including beef products may often adopt a color, odor or texture which does not accurately reflect their freshness and fitness for consumption. Consequently, the sale of such products is often inhibited as a result of such aesthetic characteristics. It may therefore be desirable to treat these products with yet another independent agent which, while it has no appreciable effect on the spoilage of the product, serves to enhance the characteristics usually deemed important for retail presentation and consumption of such. Such agents may include ascorbic acid, isoascorbic acid, erythorbic acid, lactic acid, citric acid, succinic acid or mixtures of salts thereof. Alternatively, other agents such as glycerol monolaurate, sodium sorbate, sodium acetate, sodium iodoacetate, potassium sorbate, potassium acetate, potassium iodoacetate, iodoacetomide or mixtures or acidic solutions thereof may also be used.

In yet another embodiment of the present invention, a loosely packed perishable product is positioned in a gas impermeable tray in gas communication with a first agent. In this context, "loosely packed" is defined as including optimal spacing between individual particles so as to allow substantial gaseous access to the product surface and/or as including a significant void space within the product mass. It is further desirable that the particular food product not undergo external compression and/or compaction upon loading into the package.

The product is then sealed in the package under a positive pressure. The purpose of the positive pressure is to compel gas communication between the food product and the first agent. The term "positive pressure" as used herein denotes any measurable internal package pressure greater than the external atmosphere pressure on the package but not so great as to substantially compress the product so as to decrease either its porosity or permeability.

The first agent contemplated for use with this embodiment includes such agents as $O_3$, $F_2$, $KMnO_4$, $HClO$, $ClO_2$, $O_2$, $Br_2$ or $I_2$. These agents may be combined with other gases such as $N_2$, $CO_2$ and $O_2$. The concentration of the first agent is determined by the degree of effectiveness desired by exposure, the compositional characteristics of the product, e.g., moisture content, fat content, protein content and "Asheville" content, and the amount of the product being treated. For example, a higher percentage of a stronger agent may be desired with a fresh poultry or fish product as opposed to a weaker oxidizer for use with a grain or rice product.

As earlier described, it may be desirable in some instances to introduce a second agent into the sealed package for the purposes of enhancing the overall aesthetic characteristics of the product. It is desirable that such second agent be introduced as a vapor or an aerosol and be drawn from the group consisting of ascorbic acid, isoascorbic acid, erythorbic acid, lactic acid, citric acid, succinic acid or mixtures of salts thereof.

To allow extended distribution and storage time, it may be desirable in some instances to introduce yet a third agent into gas communication with a food product. To facilitate introduction and/or subsequent extraction of the agent, it is again desirable that the third agent be introduced in gaseous or aerosol form. It is envisioned that the third agent be drawn from a group comprising glycerol monolaurate, sodium sorbate, sodium acetate, sodium iodoacetate, potassium sorbate, potassium acetate, potassium iodoacetate, iodoacetomide or mixtures or acidic solutions thereof.

In a complementary embodiment, ozone may be used to facilitate tenderness in whole muscle meat and poultry cuts and to reduce the inconsistency of the tenderness between various muscles and cuts of meat and poultry. Alternatively, ozone may be used in conjunction with nitrogen and carbon dioxide for the purpose of forming a chemically stable, cured meat color.

Example I

Ground beef trimmings (80/20) of normal pH (5.5 to 5.8) are chilled to 38° F. within 24 hours of slaughter and coarsely ground (¼" plate), mixed, and finely ground (⅛" plate). The extruded or ground product is discharged onto a conveyor belt moving at the same speed as the product flow from the grinder or extruder so that the density or compaction of the product stream is not changed. A portion sizer is used to divide the product stream into 1.5 lb. sections before the product is mechanically loaded into pre-formed polystyrene barrier MAP trays with no change in the natural shape, density or porosity of the product from that as it exited the grinder. The filled trays enter a packager where the chamber is evacuated before introduction of air containing ozone at 20 ppm or more into the chamber. After a dwell or exposure time of 15 seconds for contact between the ground beef and ozonated air, the air is evacuated and the chamber is filled with a gas mixture of 80% nitrogen and 20% carbon dioxide. The package is sealed with impermeable lidding film such that the nitrogen and carbon dioxide mixture remains inside the package during distribution and storage. The treatment of ozone completely permeates the ground beef to induce microbial inhibition and improve textural properties.

Example II

Turkeys are conventionally slaughtered and the carcasses chilled to 40° F. before hand-deboning of breasts. Breasts from 6 pounds to 12 pounds are stuffed into impermeable heat-sealed bags and water-cooked to no less than 160° F. Upon removal from the steam-heated water baths, the packages of breasts are chilled to 38° F. in a continuous mechanical brine chiller. Upon exit from the chiller, bags are manually opened and breasts are placed on conveyor belts to automatic slicing equipment, slices of 1/16 inch thickness and weighing ½ to 2 ounces are placed into impermeable film-lined plastic trays. The trays are conveyed into a chamber which is evacuated before introduction of an aerosol of 1% glycerol monolaurate and 1% sodium sorbate. After an exposure time of 3 minutes between the aerosol and the product, the chamber is evacuated and a mixture of 20% oxygen, 25% carbon dioxide and 55% nitrogen is introduced into the package immediately before heat-sealing of barrier lidding film to the tray. The treatment of this aerosol inhibits mold growth and induces maintenance of a whiter, less green color to the turkey breast slices.

Example III

Chicken carcasses are automatically deboned and skin removed to yield 2 to 3 pounds of edible muscle. The white breast portions are separated from dark breast muscle portions by line workers on each side of a conveyor belt. The white meat is conveyed into a mechanical dicer which reduces the particle size to ⅜ inch or less cubes. The cubes are conveyed into a tunnel for steam cooking to an internal temperature of no less than 165° F. before being blast chilled to 40° F. Approximately ¾ to 1 pound of chicken cubes are mechanically loaded into trays with an inner lining of impermeable film. The trays are placed into packaging equipment where, inside a chamber, the cubes are exposed to 500 ppm citric acid vapor for 30 seconds. After re-evacuation of the chamber to remove the citric acid vapor before the trays are heat-sealed with barrier film. The citric acid treatment serves to improve the shelf-life of cooked poultry by reducing lipid instability and breakdown.

Example IV

Dry (less than 14% moisture) rough or unmilled rice is shelled to result in brown rice with adhering bran coat. Two pounds of the brown rice is packaged in a gas-impermeable rigid canister, evacuated, and back-flushed with an aerosol containing 0.5% concentration of ascorbic acid. Prior to sealing the canister of rice, a pressurized gas mixture of 50% nitrogen 50% carbon dioxide is added to the canister without removal of the first ascorbic acid aerosol. The final pressure within the canister is adjusted to 20 pounds absolute (PSIA) per square inch atmospheric pressure. The packaged brown rice is stored in ambient conditions without refrigeration. The packaging method illustrated extends the usable shelf life of the brown rice by denaturing the native enzyme lipase which normally would catalyze hydrolytic oxidation of the lipids within the rice bran and suppress microbial growth which would normally occur during room temperature storage without acid treatment.

Yet another embodiment of the present invention includes a method of product preservation comprising the steps of positioning a perishable product in a selectively gas permeable package in the presence of a first gas, sealing the package with a positive package pressure, inclosing the first package in a larger package, chamber or enclosure with a higher positive pressure such that gaseous or aerosol agents within the larger container diffuse from the larger enclosure into the first package so as to enhance the appearance, organoleptic or shelf life characteristics of the perishable product.

Example V

Retail salad mix is prepared by washing lettuce before mechanical cutting into pieces of less than 2-inch length, washing carrots before mechanical shredding into slivers of less than ¼ inch diameter, and washing red cabbage which is mechanically chopped into cubes of less than ¾ inch before combining each of the ingredients in a 6:2:1 by weight proportion of lettuce, carrots and cabbage, respectively. Two pounds of salad mix is placed in a gas-impermeable semi-rigid tray. Before package closure, 0.1% erythorbic acid is introduced into contact with the salad mix and the package is heat-sealed with a lidding film permeable to carbon dioxide. A multiple of 12 trays containing salad mix are placed into an outer cardboard carton lined with a gas-impermeable liner. Prior to sealing the outer carton and liner, a pressurized gas mixture of 80% carbon dioxide and 20% nitrogen is inserted into the atmosphere surrounding the trays containing the salad mix. The final pressure within the outer carton is adjusted to 16 psi. The carton containing packages of salad mix are maintained under refrigeration conditions of 33 to 45° F. The use of erythorbic acid prevents discoloration (browning) of the salad mix, reduces vegetable tissue respiration by transpiration of the carbon dioxide into the packages at a fixed rate, and prevents deterioration by tissue dehydration thorough the impermeable nature of the master package lined carton.

Yet another embodiment of the present invention addresses the disadvantages associated with contemporary packaging and gas exchange systems. This embodiment is specifically directed to the preservation of fresh red meat, but also has general application to treatment of other perishable products.

Moisture retention is a significant problem in the transportation, preservation, and the presentation of fresh meat products. Since products are sold by weight, it is desirable that the product retain a significant liquid fraction. In this connection, beef is normally some sixty-five percent moisture. Moreover, liquid exudate, initially a bright red but later a dull red in color, is felt to significantly diminish consumer appeal at the retail level.

The liquid exudate from a meat product is generally the result of two factors. The first factor is temperature. When the product is subjected to a temperature range much above 32 degrees, exudate is released. A second cause of purge is the compression (squeezing) which generally occurs during the transportation and shipping stage of the product to the marketplace.

Contemporary modified atmosphere packaging ("MAP") techniques envision the use of a package which employs a semi-rigid bottom which is provided with one or more raised ridges along its bottom such as that disclosed and claimed in applicant's U.S. Pat. No. 4,548,824, so as to promote gas circulation about the product, and a flexible lidding film which is drawn about and coupled to the base to form a sealed chamber for the product or, alternatively, a tray within a hermetically sealed envelope. In accordance with the teachings described in U.S. Pat. Nos. 4,919,955 and 5,352,467, preparatory to retail display this chamber is filled with a gas or gas mixture to promote the oxygenation of the muscle tissues evidenced by the red bloom so valued by the consumer. It has been found, however, that while advanced gas exchange technology has enabled a dramatically enhanced shelf life for such products, this shelf life can be interrupted if the film comes in contact with the meat product. When such contact occurs, the contacted area is thereafter unable to respire and thus maintains an unattractive brownish color indicative of metmyoglobin.

Despite how tightly the lidding film is drawn initially over the tray, it will ultimately be drawn down onto the product with contemporary MAP techniques unless the product is proportionally reduced in size vis-a-vis the tray. This occurs because the myoglobin pigment becomes oxygenated and oxygen and carbon dioxide becomes dissolved in the water phase of the meat product during the shelf presentation period. When these gases are absorbed, a semi vacuum is created in the product chamber thereby downwardly distorting the film. It has been observed that this phenomena is so pronounced in packages utilizing lidding films that a product with a projected 10–12 day shelf life must not exceed 50 percent of the package volume.

The methodology of the present invention allows the preservation of a substantial portion of this headroom by addressing this gas absorption phenomena so as to allow a fill exceeding 90 percent with a projected 15 to 20 day shelf life.

This method envisions reducing the product to a temperature range of some 26–36° F., and thereafter introducing a chilled gas mixture to prepare the meat product for a subsequent oxygenation step. In one preferred embodiment, this mixture consists of a carbon dioxide and nitrogen mixture in a proportional range of 15–85% nitrogen and at least 15% carbon dioxide. Other inert gases such as argon or krypton are also envisioned within the spirit of the present invention. It is also contemplated that a hydrogen fraction, e.g. 1% may also be added to the mixture. These gases are introduced into the package at a temperature range of 26–36° F. and at a positive gas pressure of 5–60 millibars for a significant residence time to promote penetration of the gas mixture into the product. The void fraction of the ground meat or intact meat portion is then reduced.

In another embodiment, a chilled gas mixture comprising from 70–85% inert gas and 15–30% carbon dioxide is chilled to some 20–36° F. and introduced into a sealed container about the product at a positive pressure of between 5–60 millibars. This chilled gas may include a carbon monoxide fraction or an oxidizer, e.g. ozone mixtures.

The chilled gas may be replaced by a second gas containing a significant oxygen fraction to promote a bloom of the product. This exchange or flushing of the first gas may be accomplished in a number of ways. One such way is to utilize a container including a selectively permeable film. This may be accomplished, for example, by using a selectively permeable film situated beneath a removable impermeable film. The removable film may be removed, thereby allowing gases to exchange with the meat product. This process may be enhanced where the gas is mechanically flushed through the permeable film.

This gas is introduced at any stage prior to display. The effect of this procedure is to block many of the respiration sites on the surface of the product for an average depth of 6–7 mm. As a result, the gas mixture containing an oxygen and carbon dioxide fraction accompanying the product is not so readily absorbed into the product so as to create a vacuum, thus inadvertent contact between the lidding film and the product is thereby avoided.

The introduction of this gas mixture under slight positive pressure also serves to stabilize the meat product as to water activity so as to minimize the undesired exudate. Evaporation of moisture begins on the product surface and as the surface dries, surface moisture is replenished by osmosis. The drying power of gas is dependent on temperature, relative humidity and speed of gas movement. The method of the present invention equalizes product and gas temperature, slows and/or interrupts respiration, and minimizes relative humidity change from moist product to dry environment. The positive pressure utilizing these gases, particularly enriched carbon dioxide, in the specified temperature ranges of gas and product changes the osmotic pressure of both muscle and fat tissue of a meat product impeding or retarding outward liquid movement. This phenomena occurs within a narrow cold temperature range allowing meat products the greatest beneficial effects without subjecting them to the harmful effects of freezing the tissue.

The final step of the proposed process involves the exchange of the preparatory atmosphere and replacement with a second gas rich in oxygen. This may be accomplished by using a variety of techniques such as those disclosed in U.S. Pat. No. 5,481,852. Alternatively, this may be accomplished by utilizing gas flush packaging. Still alternatively, it is contemplated that a package may be used which contains a removable outer film or a valve which may be opened on site to allow the introduction of an oxygenated atmosphere into the product package.

In yet an alternative embodiment, it is also envisioned that a tri-gas atmosphere consisting of nitrogen, carbon dioxide and oxygen, or other inert gases, may be used as the second gas. Nitrogen, being inert, is basically a filler preventing negative pressure package collapse as the other two gases are reactive and the products, in addition to any micro flora present, are dynamic and continue respiring and metabolizing. The enriched carbon dioxide fraction continues the minimization of water activity started in the initial phase plus retardation of microbial growth. The enriched oxygen fraction introduces the advantages of oxygenation to muscle and fat tissue. It is further envisioned that carbon monoxide may be used to produce a red bloom in some products. Carbon monoxide is known to maintain color in red meat products when used as a fraction of gas mixtures but is not permitted by FDA regulations for use in red meat packaging. Current regulations allow up to 4% carbon monoxide as a component in modified atmospheres for retardation of lettuce core browning in its distribution.

In another embodiment a perishable product is sealed within a container and then chilled to between 26–36 Fahrenheit. This product may comprise any food or food product subject to deterioration but ideally comprises an emulsion of muscle tissue, fat, water and a binding agent, e.g. a grain derivative. The chilled product is then exposed to a chilled gas mixture comprising a combination of inert gas including at least 15% carbon dioxide gas and at least 45% oxygen. Alternatively, this mixture may comprise $CO_2$. The chilled gas is introduced and maintained about the product at a positive pressure for a selected residence time to promote penetration of the gas mixture into the product.

The chilled gas may be introduced via a variety of means including through a selectively permeable film comprising a portion of the package. In one embodiment, a two component film may be used, where the bottom film closest to the product is selectively permeable while the outer layer is substantially gas impermeable so as to prevent gas communication between the product and the environment. The outer layer may be removed prior to display so as to promote the "bloom" in meat cuts favored by consumers. For fish, poultry and other products, the outer layer may be retained.

An additional step may include placing an oxygen-exchanging material in the package to initially absorb free oxygen. As an optional and subsequent step, the chilled gas may be replaced with a second gas having a significant oxygen fraction so as to enhance the "bloom" of the product.

In another embodiment, a raw meat, poultry or fish product is treated exposing the raw product to an anaerobic environment within a sealed container, chilling the product to between 26–42° F., subsequently removing the product from the container, fabricating the product and thereafter packaging the fabricated product in a sealed gas impermeable container, e.g. a vacuum package. This basic process may include a variety of other steps including vacuum packaging the product for a selected residence time. Alternatively, a gas mixture including an oxygen component may be introduced into the second container so as to produce oxygenoglobin. This gas mixture may also include carbon monoxide and an oxidizer, e.g. ozone. Alternatively, this gas mixture may be anoxic, comprising some 70–85% inert gas and 15–30% carbon dioxide.

This gas mixture may be replaced mechanically by a second gas by flushing or by use of and subsequent removal of films of varying permeabilities as described above. Still alternatively, the product may be exposed to a mixture of inert gas and carbon dioxide introduced at ambient pressure into the second package.

Still another embodiment contemplates a process whereby the pigment enzymes in the product are stabilized in a substantially anaerobic environment. This process contemplates chilling the product to between 22–42° F., maintaining the product in a substantially anaerobic environment within a sealed container, removing the product from the container and thereafter repackaging the product in a second, gas impermeable container. In this embodiment, a second gas containing on oxygen-rich component, e.g. 65–80% oxygen, 15–30% carbon dioxide may be introduced into the second container. This later added mixture may also contain inert gas.

In yet an alternative embodiment, it is also envisioned that a tri-gas atmosphere consisting of nitrogen, carbon dioxide and oxygen, or other inert gases, may be used as the second gas. Nitrogen, being inert, is basically a filler preventing negative pressure package collapse as the other two gases are reactive and the products, in addition to any micro flora present, are dynamic and continue respiring and metabolizing. The enriched carbon dioxide fraction continues the minimization of water activity started in the initial phase plus retardation of microbial growth. The enriched oxygen fraction introduces the advantages of oxygenation to muscle and fat tissue. It is further envisioned that carbon monoxide may be used to produce a red bloom in some products. Carbon monoxide is known to maintain color in red meat products when used as a fraction of gas mixtures but is not permitted by FDA regulations for use in red meat packaging. Current regulations allow up to 4% carbon monoxide as a component in modified atmospheres for retardation of lettuce core browning in its distribution.

Other embodiments of the present invention envision the use of a package having a prepunched aperture to which is applied a resealable label. Other embodiments envision a valveless package design where gas exchange is conducted through a hole made in the package wall, where desired package pressure is maintained by a pressure sensitive label or resealable film. Other embodiments envision a valve which is opened or closed via the introduction of an external power source, e.g. a microwave power source, an electrical charge, a light beam or a focused heat beam.

Still other embodiments contemplate the use of a chemical reaction to evacuate a given mass of gas from within a sealed receptacle, such as a chemical which can be destabilized upon the introduction of an external power source, e.g. a microwave. Other embodiments contemplate the use of an internal packer package with a sufficient void space to enable product oxygenation. Another embodiment contemplates a prepunched package which includes two, oppositely disposed holes to enable gas flushing gas exchange with labels applied over apertures formed in the packages, thereby creating a positive pressure.

Yet another embodiment contemplates the use of a non-compacted ground meat beginning product of selected densities, water content and the like so as to be susceptible to the creation of a desired hemoglobin or myoglobin reaction upon the introduction of a gas to the product under positive pressure. This is illustrated where a less expensive meat product is desired and produced by adding additional water and binding agents. This embodiment is exemplified by the addition of water to the ground meat product with the use of certain grain flour derivatives.

Yet another embodiment of the invention includes treating a perishable fruit or vegetable product, e.g. apricots, lettuce or apples, so as to retard spoilage and enable greater transit time and shelf life. In this embodiment, the fruit product is placed in a container which is then sealed. Such a container may comprise a sealable railroad car, seagoing container or a crate suitable for transport on truck. The product is then tempered by adjusting its temperature to between 45–80° F. A humidified, tempered gas mixture is then introduced into the container at a temperature between 36–45° F., where the mixture preferably comprises a mixture of inert gases, e.g., nitrogen, carbon dioxide and ethylene. This gas mixture is introduced in one of the manners discussed above in the relation to other embodiments, and is maintained about said product at a positive pressure for a residence time sufficient to delay oxidation and dehydration of the product. The residence time will vary depending on the product.

Yet another embodiment contemplates the treatment of a perishable egg product in the shell to promote shelf life. This method includes the steps of sealing the egg product in a container and then chilling the product to between 40–65° F. A chilled, humidified gas mixture is then introduced into the container where the mixture includes a combination of inert gases, e.g. nitrogen and carbon dioxide. This gas is preferably maintained at a positive pressure and for a selected residence time to reduce dehydration and weight loss.

Although particular detailed embodiments of the apparatus and method have been described herein, it should be understood that the invention is not restricted to the details of the preferred embodiment. Many changes in design, composition, configuration and dimensions are possible without departing from the spirit and scope of the instant invention.

What is claimed is:

1. A method for treating perishable meat products within a sealed container, comprising:
   chilling the product to between 26–36° F.;
   exposing the chilled product to a chilled gas mixture to slow the respiration of the muscle tissue where said mixture comprises a combination of an inert gas and at least 15 percent carbon dioxide, where further said gas mixture is introduced to and maintained about said product at a positive pressure for a selected residence time to achieve penetration of said mixture into the meat product.

2. The method of claim 1 further including the step of replacing said chilled gas mixture with a second gas having a significant oxygen fraction.

3. The method of claim 1 where said chilled gas mixture is introduced at a temperature range of between 26 and 36° F.

4. The method of claim 1 where said chilled gas mixture is introduced during the initial packing stage of the meat product.

5. The method of claim 1 where said inert gas is nitrogen.

6. The method of claim 1 where said inert gas is selected from the group consisting of the noble gases.

7. The method of claim 1 where the chilled gas mixture is introduced at a positive pressure of between 5 to 60 millibars.

8. The method of claim 1 where the residence time is that time sufficient to establish an average penetration of the chilled gas into an intact tissue of some 5–7 mm.

9. The method of claim 1 where the residence time is that time sufficient to establish a complete penetration of a ground meat product.

10. The method of claim 2 where said second gas is comprised of oxygen and carbon dioxide.

11. The method of claim 2 where said second gas includes carbon monoxide.

12. The method of claim 1 where said gas mixture comprises a combination of inert gas and at least 15% carbon dioxide and 1% hydrogen.

13. The method of claim 1 further including the step of reducing the void fraction of the ground meat product or intact meat portion.

14. A method for treating perishable meat products within a sealed container, where said method is adapted to reduce the liquid exudate from the product, comprising:
   chilling the product to a temperature between 26–36° F.;
   exposing the product to a chilled gas mixture comprising from 70 to 85% inert gas and 15 to 30% carbon dioxide, where such gas is introduced at a temperature range of between 20–36° F., where further this chilled gas mixture is introduced at a positive pressure between 5–60 millibars.

15. The method of claim 14 further including the step of introducing a second gas to induce a bloom of the product.

16. The method of claim 14 where the chilled gas also includes carbon monoxide.

17. The method of claim 14 where the chilled gas includes an oxidizer.

18. The method of claim 17 where the oxidizer includes ozone and mixtures including ozone as a component.

19. The method of claim 14 further including the step of replacing the chilled gas with a second gas by flushing said second gas through the sealed container.

20. The method of claim 12 wherein the gas is flushed through a resealable valve.

21. The method of claim 19 where said container is at least partially comprised of a permeable film where the permeability of the film is mechanically induced.

22. The method of claim 12 wherein the gas is flushed through a selectively permeable film.

23. A method for treating perishable meat products within a sealed container, where said container includes a tray and a selectively impermeable lid, comprising:
   chilling the meat product to between 26–36° F.:
   exposing the chilled product to a chilled gas mixture to slow the respiration of the muscle tissue where said mixture comprises a combination of an inert gas and at least 15% carbon dioxide, where further said gas is introduced to and maintained about said meat product at a positive pressure for a selected residence time to promote penetration of said gas into the meat product and to achieve conversion from deoxymyoglobin to oxymyoglobin when meat product is exposed to oxygen.

24. The method of claim 23 further including the step of replacing the chilled gas mixture with a second gas.

25. The method of claim 23 where said sealed container at least partially comprises a tray and a selectively permeable lid where said permeable lid comprises a gas impermeable outer film layer and a gas permeable inner layer, where the combination is sealed to the tray.

26. The method of claim 25 where said chilled gas mixture is introduced through said inner film layer by removing said outer film layer.

27. The method of claim 24 where said second gas includes a significant oxygen fraction.

28. A method for treating a perishable product comprising the steps of:
   sealing the product within a container;
   chilling the product to between 26–36° F.;
   exposing the chilled product to a chilled gas mixture to slow the respiration of the muscle tissue where said mixture comprises a combination of inert gas, at least 15% carbon dioxide, and at least 45% oxygen, where further said gas is introduced to and maintained about said product at a positive pressure for a selected residence time to promote penetration of the gas mixture into the meat product.

29. The method of claim 28 where said gas mixture; is introduced through a selectively permeable film forming the lid on the container.

30. The method of claim 28 where the product includes an emulsion of muscle tissue, fat, water and a binding agent.

31. The method of claim 30 where the binding agent is a grain derivative.

32. A method of treating a perishable fruit product including the steps of:
sealing the fruit product within a container;
tempering the product to between 45–80° F.;
introducing a tempered and humidified gas mixture into the container to slow the ripening process where said mixture comprises a combination of inert gases, where said gas mixture is maintained about said product for a selected residence time to delay oxidation and dehydration of said product.

33. The method claim 32 where said gas mixture includes nitrogen, carbon dioxide and ethylene.

34. A method for treating an egg product comprising the steps of:
sealing the egg product within a container;
chilling the egg product to between 40–65° F.;
introducing a chilled and humidified inert gas mixture into said container, where said gas mixture is maintained about said product at a positive pressure for a selected residence time.

35. The method of claim 34 where said gas mixture includes nitrogen and carbon dioxide.

36. A method for treating a raw meat, poultry or fish product so as to stabilize and equilibrate pigment enzymes in said product, comprising the steps of:
exposing the raw product to an anaerobic environment within a sealed, first container;
chilling the product to a temperature between 26–42° F.;
removing said product from said container;
fabricating said product; and
packaging said fabricated product in a second, sealed gas impermeable container.

37. The method of claim 36 further including the step of vacuum packaging the product for a selected residence time.

38. The method of claim 36 further including the step of introducing oxygen into the second container so as to produce oxymyoglobin.

39. The method of claim 36 further introducing the step of exposing the product to a mixture of inert gas and carbon dioxide.

40. The method of claim 39 where said mixture is introduced at ambient pressure.

41. The method of claim 36 further including the step of introducing a second gas to induce a bloom of the product.

42. The method of claim 41 where the second gas includes carbon monoxide.

43. The method of claim 41 where the second gas includes an oxidizer.

44. The method of claim 43 where the oxidizer includes ozone as a component.

45. The method of claim 38 including the step of replacing the first gas with a second gas by flushing the second gas through the sealed container.

46. The method of claim 45 where said second gas is flushed through a resealable valve.

47. The method of claim 45 where the sealed container includes a impermeable film sealed about a permeable film where the impermeable film is removed so as to allow the product exposure to the atmosphere through the permeable film while in the sealed container.

48. The method of claim 36 where the second gas mixture is introduced at a pressure greater than ambient pressure.

49. The method of claim 36 where said sealed container consists of a dual barrier of an inner permeable barrier and an outer impermeable barrier.

50. The method of claim 36 further including the step of introducing an anoxic gas mixture in said second package.

51. The method of claim 50 where said anoxic gas is 70–85% inert gas and 15–30% carbon dioxide.

52. The method of claim 50 where said anoxic gas is carbon dioxide.

53. A method for treating a perishable meat product within a sealable container such that the pigment enzymes in said product are stabilized and equilibrated in a substantially anaerobic environment while said product exists in a coarse, ground state, the method comprising the steps of:
chilling the product to a temperature between 22–42° F.;
maintaining the product in a substantially anaerobic environment within a first sealed container;
removing the product from the container; and
repackaging the product in a second, gas impermeable container.

54. The method of claim 53 further including the step of exposing the product while in the second container to a mixture of carbon dioxide and inert gas where this mixture is introduced at positive pressure.

55. The method of claim 53 further including the step of introducing a second gas into said second container to induce a bloom of said product.

56. The method of claim 55 where said gas mixture comprises between 65–80% oxygen and 15–30% carbon dioxide.

57. The method of claim 56 further including an inert gas.

58. A method for treating a perishable meat product within a sealable container comprising the steps of:
placing the product in a substantially anaerobic environment for a selected period of time; preparing the product for introduction to an oxygen containing atmosphere where said preparation includes the steps of:
chilling the product to a temperature between 22–42° F.;
removing the product from the container;
fabricating the product by cutting or grinding; and
repackaging the product in a second, gas impermeable container.

* * * * *